(12) United States Patent
Pawsey et al.

(10) Patent No.: US 9,375,565 B2
(45) Date of Patent: Jun. 28, 2016

(54) STIMULATING ASSEMBLY FIXATION FEATURES

(71) Applicants: Nicholas Charles Kendall Pawsey, North Ryde (AU); Frank Risi, Newtown (AU)

(72) Inventors: Nicholas Charles Kendall Pawsey, North Ryde (AU); Frank Risi, Newtown (AU)

(73) Assignee: Cochlear Limited, Macquarie University, NSW (AU)

( * ) Notice: Subject to any disclaimer, the term of this patent is extended or adjusted under 35 U.S.C. 154(b) by 84 days.

(21) Appl. No.: 14/064,586

(22) Filed: Oct. 28, 2013

(65) Prior Publication Data

US 2015/0119967 A1 Apr. 30, 2015

(51) Int. Cl.
*A61N 1/05* (2006.01)
*A61N 1/36* (2006.01)

(52) U.S. Cl.
CPC .......... *A61N 1/0541* (2013.01); *A61N 1/36032* (2013.01)

(58) Field of Classification Search
CPC .......... A61N 1/0541; A61N 1/36032
See application file for complete search history.

(56) References Cited

U.S. PATENT DOCUMENTS

| | | | |
|---|---|---|---|
| 5,653,742 A | 8/1997 | Parker et al. | |
| 6,321,125 B1 * | 11/2001 | Kuzma | 607/137 |
| 6,889,094 B1 | 5/2005 | Kuzma et al. | |
| 2002/0029074 A1 | 3/2002 | Treaba et al. | |
| 2003/0069613 A1 | 4/2003 | Kuzma et al. | |
| 2008/0154339 A1 | 6/2008 | Carter | |
| 2008/0234793 A1 | 9/2008 | Gibson | |
| 2009/0254163 A1 | 10/2009 | Gibson | |
| 2011/0295352 A1 * | 12/2011 | Thenuwara et al. | 607/137 |
| 2012/0271393 A1 | 10/2012 | Schleicher et al. | |

FOREIGN PATENT DOCUMENTS

WO 2008058232 A2 5/2008

OTHER PUBLICATIONS

International Search Report and Written Opinion in corresponding International Application No. PCT/IB2014/065587, mailed Feb. 13, 2015, 11 pages.

* cited by examiner

*Primary Examiner* — Joseph Dietrich
(74) *Attorney, Agent, or Firm* — Edell, Shapiro & Finnan, LLC

(57) ABSTRACT

Embodiments presented herein are generally directed to a stimulating assembly of a cochlear implant. The stimulating assembly comprises one or more fixation features configured to be inserted into a recipient's cochlea via an opening in the cochlea. Following insertion, the one or more fixation features are configured to engage an inner surface of the cochlea adjacent to the opening to prevent movement of the stimulating assembly out of the cochlea through the opening.

19 Claims, 17 Drawing Sheets

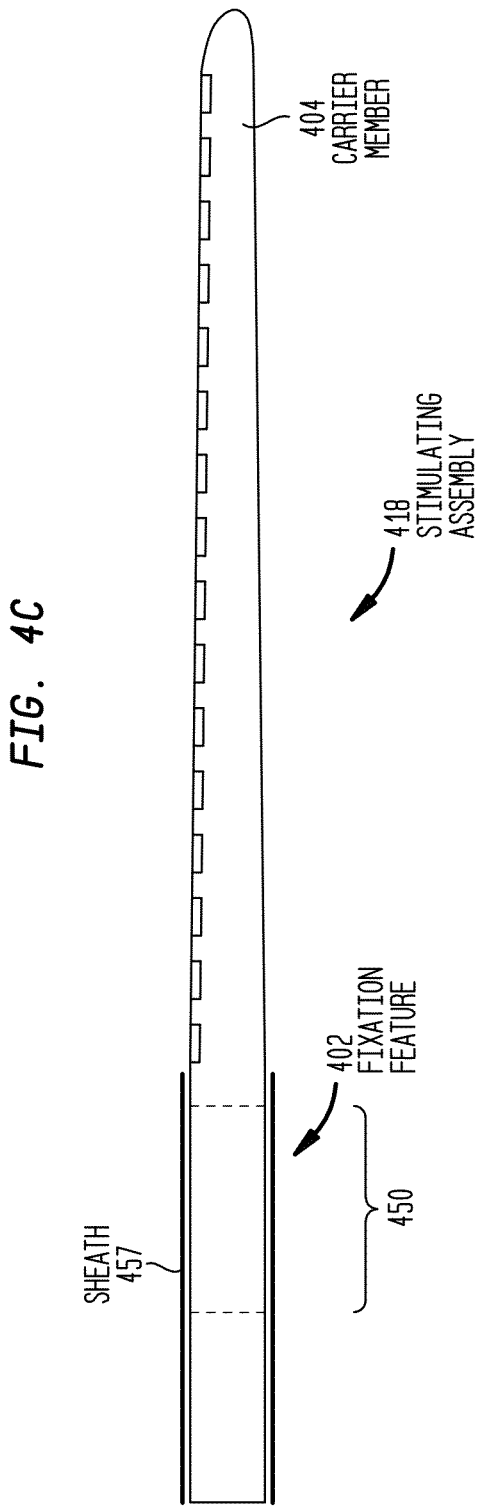

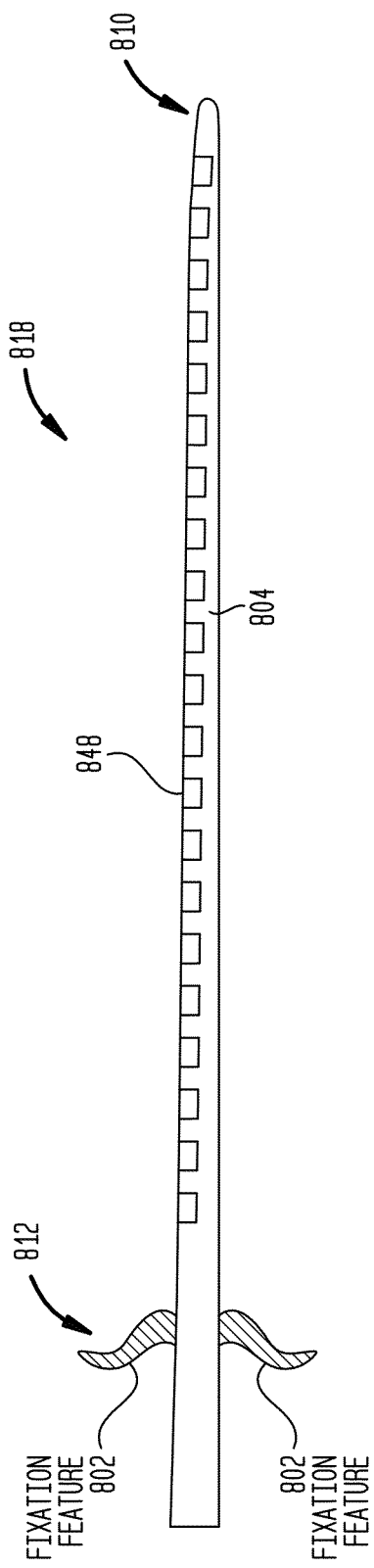

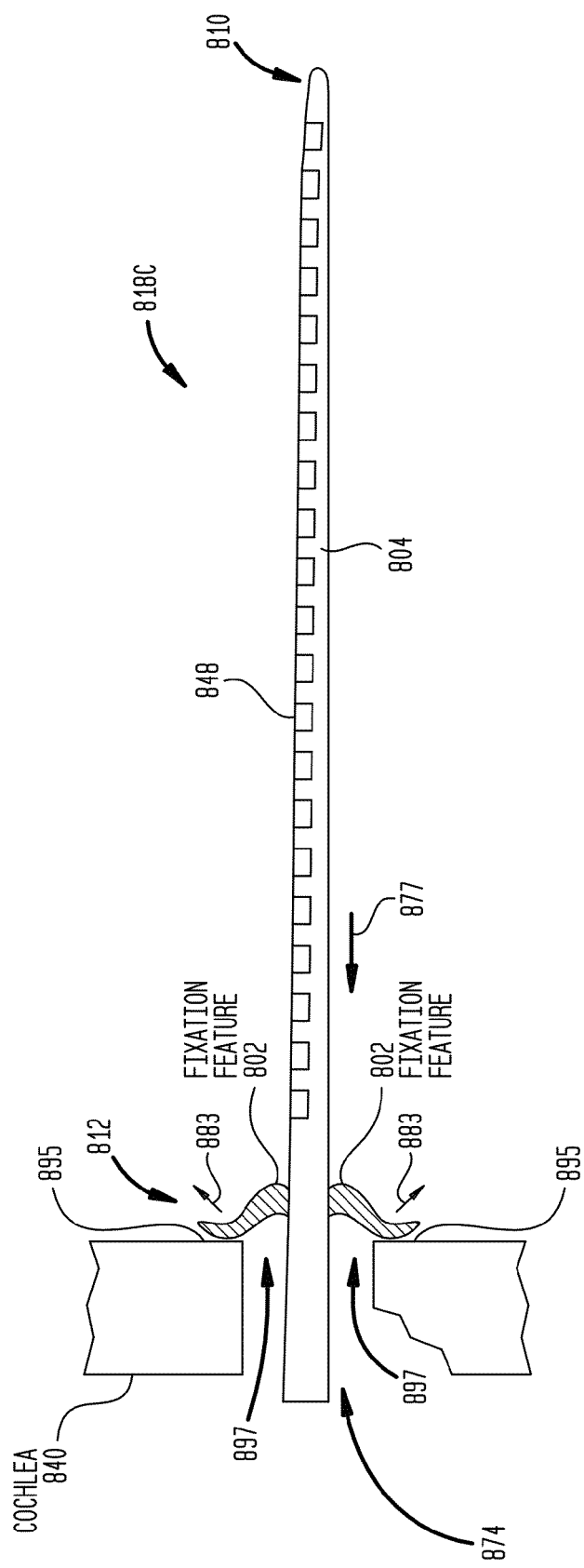

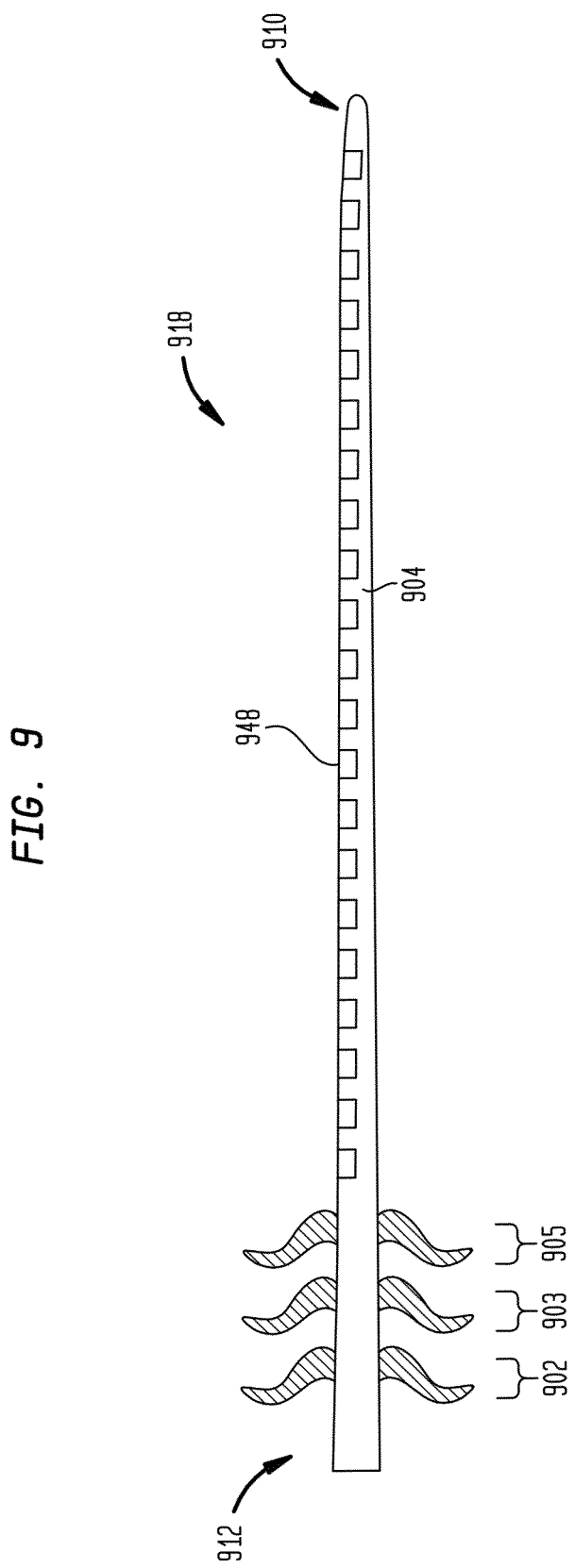

STIMULATING ASSEMBLY FIXATION FEATURES

BACKGROUND

1. Field of the Invention

The present invention relates generally to an implantable stimulating assembly, and more particularly, to stimulating assembly fixation features.

2. Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect of the invention, a stimulating assembly for insertion into a cochlea of a recipient through an opening in the cochlea is provided. The stimulating assembly comprises an elongate carrier member having a proximal end and a distal end and a plurality of stimulating contacts disposed along at least a first surface of the carrier member. A fixation feature is formed in the proximal end of the carrier member and is configured to, after insertion into the cochlea; prevent movement of the stimulating assembly out of the cochlea through the opening.

In one aspect of the invention, an apparatus is provided. The apparatus comprises an elongate carrier member having first and second distally extending portions and a plurality of stimulating contacts disposed along at least a first surface of the second portion. The carrier member comprises a transition region having a shape such that the second portion of the elongate carrier member is offset from the first portion of the carrier member.

In another aspect of the invention, a stimulating assembly for insertion into a cochlea of a recipient through an opening in the cochlea is provided. The stimulating assembly comprises an elongate carrier member having a proximal portion and a distal portion, a plurality of stimulating contacts disposed along at least a first surface of the distal portion, and a fixation feature comprising a portion of the carrier member formed into a zigzag shape such that the distal portion of the elongate carrier member is offset from the proximal portion of the carrier member.

BRIEF DESCRIPTION OF THE DRAWINGS

Embodiments of the present invention are described herein in conjunction with the accompanying drawings, in which:

FIG. 4C is a side view of the stimulating assembly of FIG. 4A with a straightening sheath in accordance with embodiments of the present invention;

FIG. 8A is a side view of another stimulating assembly comprising fixation features in accordance with embodiments of the present invention;

FIG. 8C is a side view of the stimulating assembly illustrated in FIG. 8A following insertion into a recipient's cochlea; and FIG. 9 is a side view of a stimulating assembly comprising a plurality of fixation features in accordance with embodiments of the present invention.

DETAILED DESCRIPTION

Embodiments presented herein are generally directed to a stimulating assembly of a cochlear implant (also commonly referred to as cochlear implant device, cochlear prosthesis, and the like; simply "cochlear implant" herein). The stimulating assembly comprises one or more fixation features configured to be inserted into a recipient's cochlea via an opening in the cochlea. Following insertion, the one or more fixation features are configured to engage an inner surface of the cochlea adjacent to the opening to prevent movement of the stimulating assembly out of the cochlea through the opening.

Figure 1:
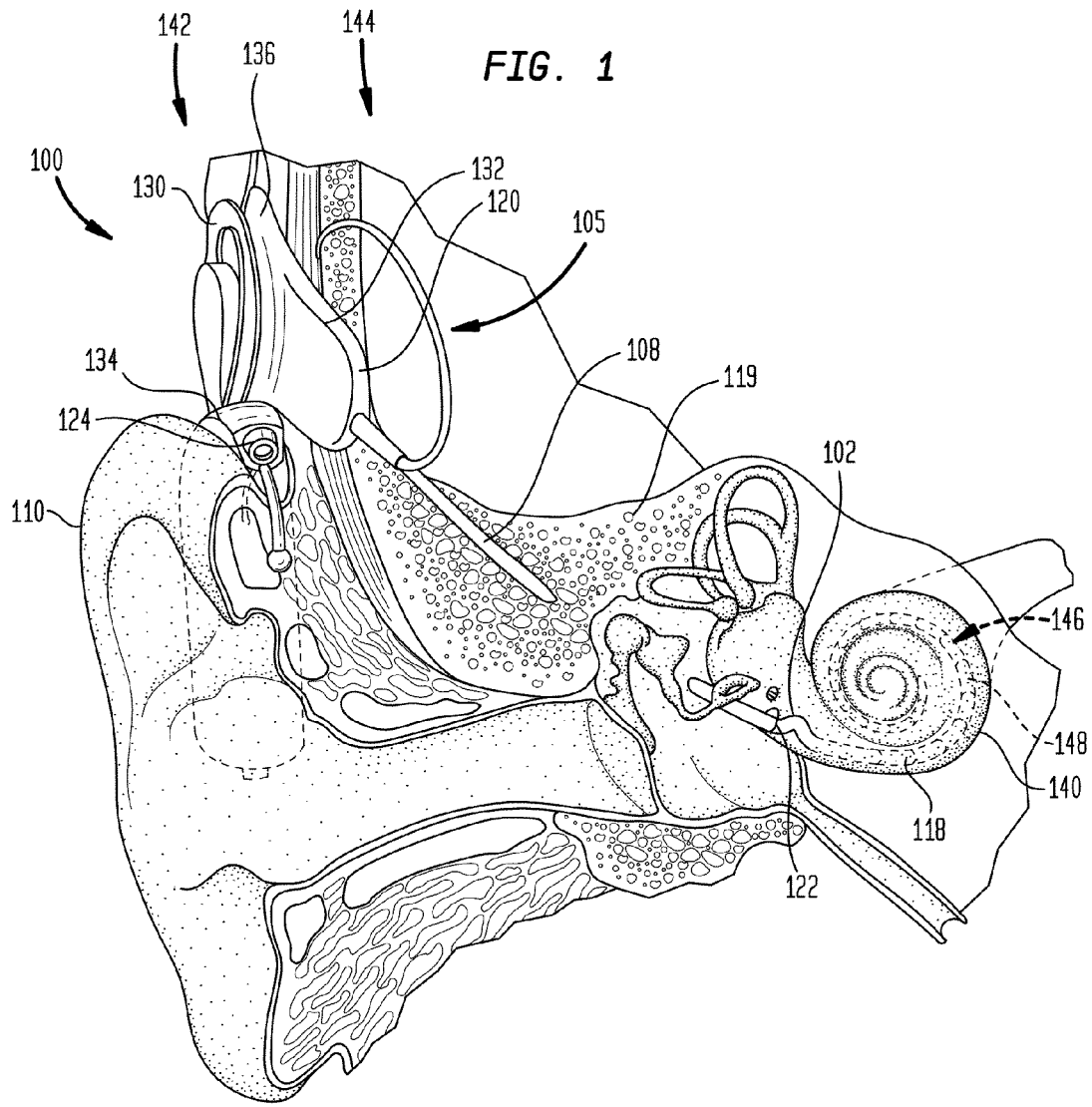
FIG. 1 is a schematic diagram of an implanted cochlear implant comprising a stimulating assembly having a fixation feature in accordance with embodiments presented herein.

FIG. 1 is perspective view of an exemplary cochlear implant 100 in accordance with embodiments presented herein. The cochlear implant 100 includes an external component 142 and an internal or implantable component 144. The external component 142 is directly or indirectly attached to the body of the recipient and typically comprises one or more sound input elements 124 (e.g., microphones, telecoils, etc.) for detecting sound, a sound processor 134, a power source (not shown), an external coil 130 and, generally, a magnet (not shown) fixed relative to the external coil 130. The sound processor 134 processes electrical signals generated by a sound input element 124 that is positioned, in the depicted embodiment, by auricle 110 of the recipient. The sound processor 134 provides the processed signals to external coil 130 via a cable (not shown).

The implantable component 144 comprises an implant body 105, a lead region 108, and an elongate stimulating assembly 118. The implant body 105 comprises a stimulator unit 120, an internal coil 136, and an internal receiver/transceiver unit 132, sometimes referred to herein as transceiver unit 132. The transceiver unit 132 is connected to the internal coil 136 and, generally, a magnet (not shown) fixed relative to the internal coil 136. Internal transceiver unit 132 and stimulator unit 120 are sometimes collectively referred to herein as a stimulator/transceiver unit 120.

The magnets in the external component 142 and implantable component 144 facilitate the operational alignment of the external coil 130 with the internal coil 136. The operational alignment of the coils enables the internal coil 136 to transmit/receive power and data to/from the external coil 130. More specifically, in certain examples, external coil 130 transmits electrical signals (e.g., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding. In use, transceiver unit 132 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is implanted in cochlea 140 and includes a contact array 146 comprising a plurality of stimulating contacts 148. Stimulating assembly 118 extends through cochleostomy 122 and has a proximal end connected to stimulator unit 120 via lead region 108 that extends through mastoid bone 119. Lead region 108 couples the stimulating assembly 118 to implant body 105 and, more particularly, stimulator/transceiver unit 120. The stimulating contacts 148 may be electrical contacts, optical contacts, or a combination of optical and electrical contacts. Present commercial devices offered by the industry use electrical contacts, but Cochlear and others are engaged in research on the potential uses of optical stimulation alone of in conjunction with electrical or other stimulation mechanisms.

There are a variety of types of intra-cochlear stimulating assemblies that may be inserted into a recipient's cochlea. For example, a perimodiolar stimulating assembly is a stimulating assembly that is configured to adopt a curved configuration during and/or after implantation into the recipient's cochlea. To achieve this, the stimulating assembly may be pre-curved to the same general curvature of a cochlea. Perimodiolar stimulating assemblies are typically held straight by, for example, a stiffening stylet or sheath which is removed during implantation. Varying material combinations or shape memory materials may also be used so that the stimulating assembly may adopt its curved configuration when in the cochlea.

A stimulating assembly can also be a non-perimodiolar stimulating assembly. A non-perimodiolar stimulating assembly may be a substantially straight assembly, a mid-scala assembly which assumes a mid-scala position during or following implantation, or a short assembly implanted into at least a basal region of the cochlea. The stimulating assembly may extend towards the apical end of the cochlea, referred to as the cochlea apex.

In certain circumstances a stimulating assembly may extrude (i.e., migrate/withdraw) from a recipient's cochlea. Extrusion of a stimulating assembly may negatively impact hearing performance of the stimulating assembly. As such, in the embodiments of FIG. 1, a fixation feature 102 is disposed near a proximal end of the stimulating assembly 118. The fixation feature 102 is configured to be inserted through the cochleostomy 122 and, following insertion, engage an inner surface of the cochlea 140 adjacent to the cochleostomy 122 to prevent extrusion of the stimulating assembly out of the cochlea 140.

Figure 2A:
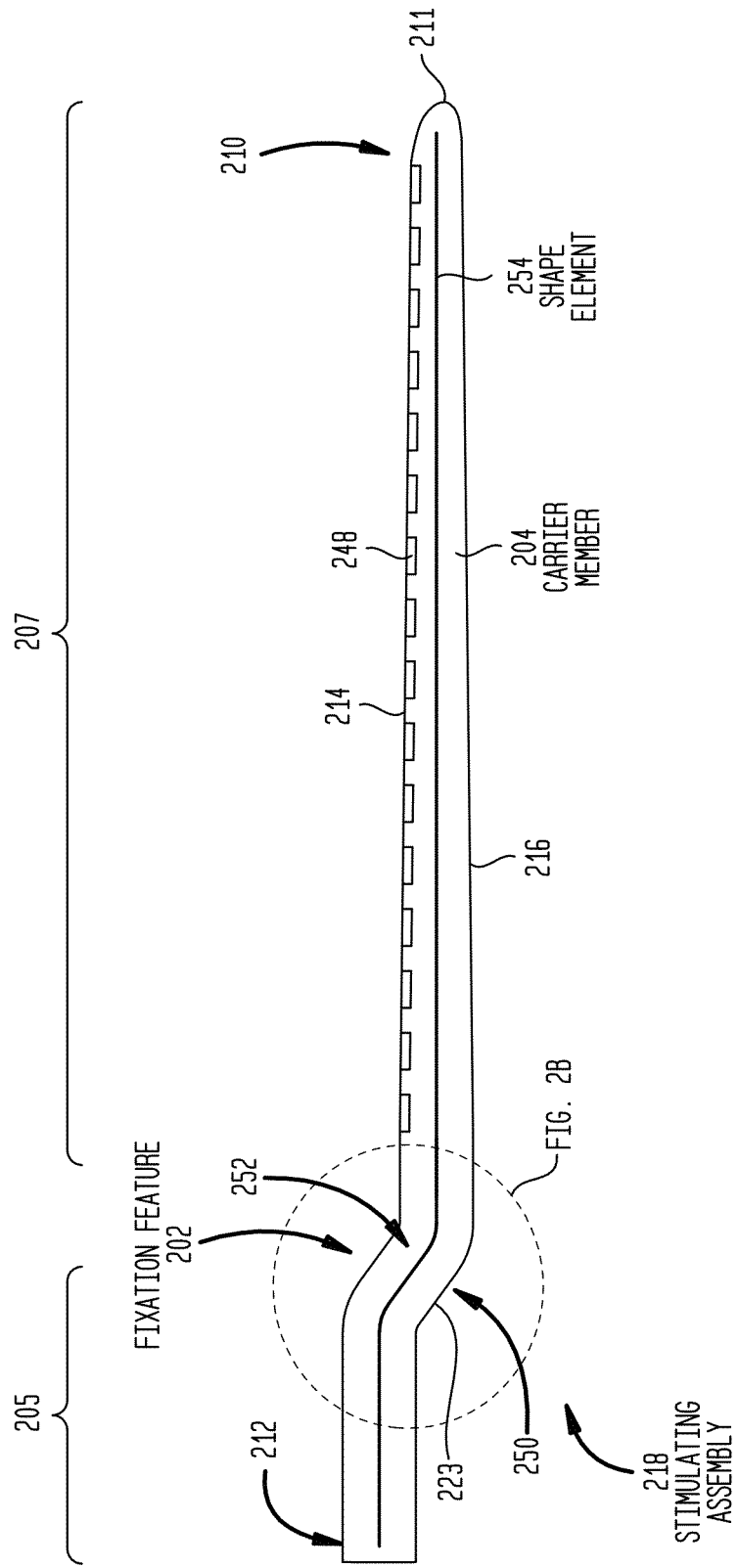
FIG. 2A is a side view of a stimulating assembly comprising a fixation feature in accordance with embodiments of the present invention.
Figure 2B:
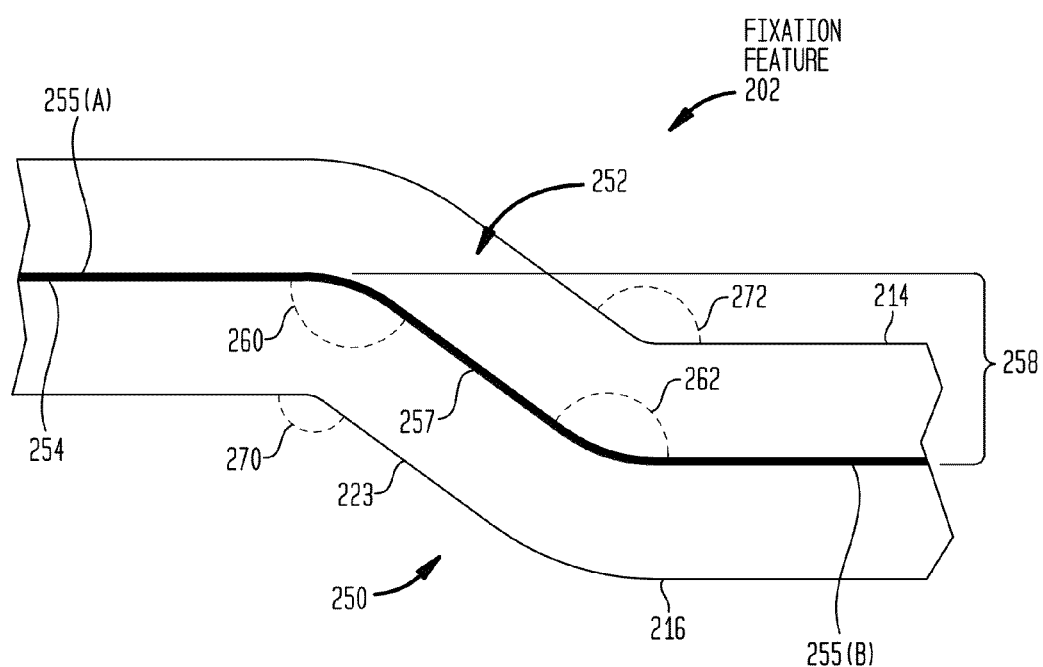
FIG. 2B is an enlarged view of the fixation feature of the stimulating assembly illustrated in FIG. 2A.
Figure 2C:
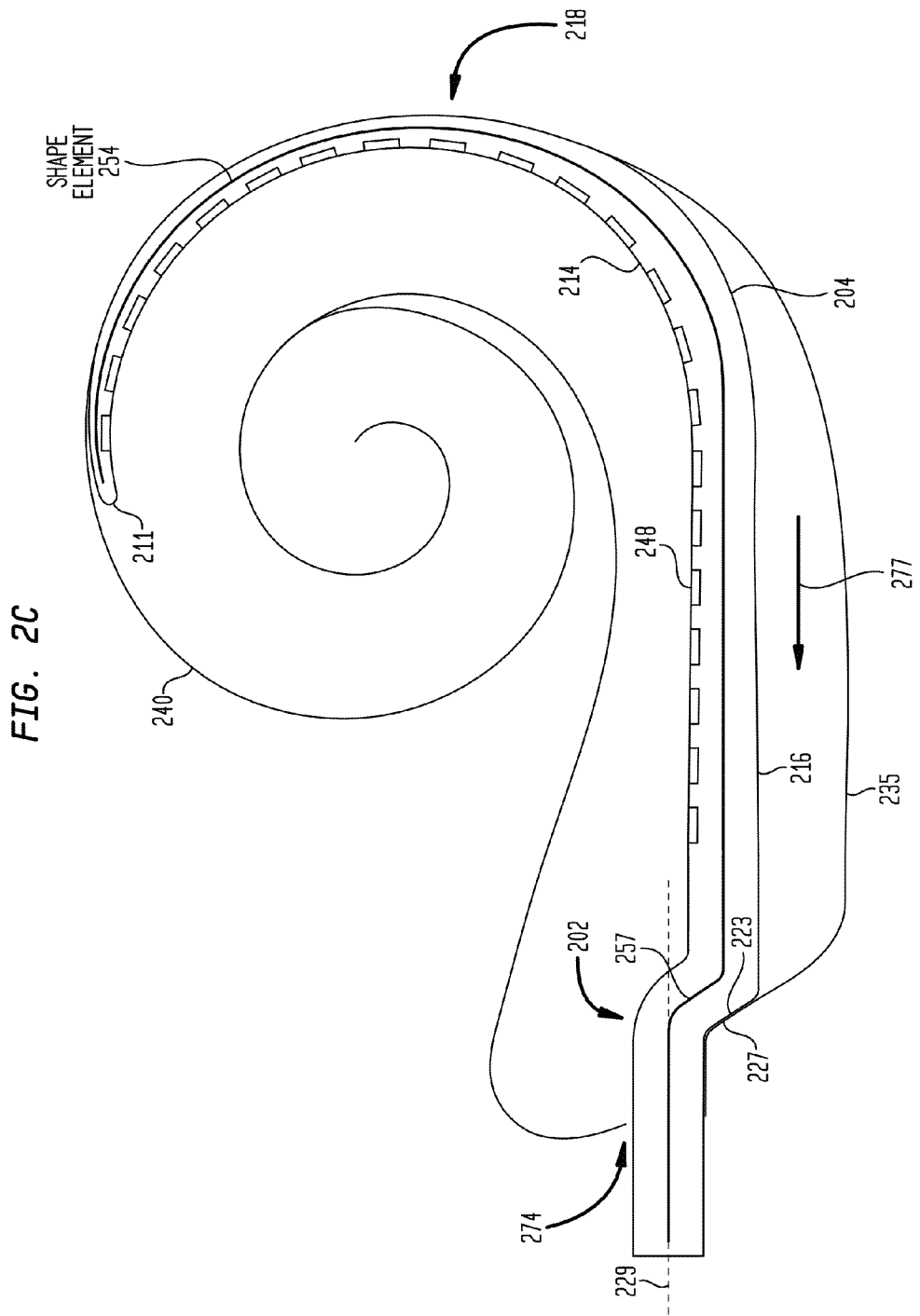
FIG. 2C is a side view of the stimulating assembly illustrated in FIG. 2A following insertion into a recipient's cochlea.

FIGS. 2A-2C are side views of a stimulating assembly 218 that comprises a fixation feature 202 in accordance with embodiments presented herein. FIG. 2A illustrates stimulating assembly 218 prior to insertion into a recipient's cochlea, while FIG. 2B illustrates an enlarged view of the fixation feature 202 prior to insertion. FIG. 2C illustrates electrode assembly 218 after insertion when the fixation feature 202 is positioned to substantially prevent extrusion/migration of the stimulating assembly 218 out of the recipient's cochlea 240.

Stimulating lead assembly 218 comprises a carrier member 204 having a distal end 210 and a proximal end 212. Distal end 210 terminates in a tip 211 that is adapted to be implanted furthest into the recipient's cochlea 240. A plurality of spaced stimulating contacts 248 are mounted or disposed in/on at least a first surface 214 of the carrier member 204 between the proximal end 212 and the distal end 210. It should be appreciated that as used herein, particular combinations of the terms mounted/disposed, in/on, etc., are not to be interpreted to refer to any particular manufacturing technique or structural relationship.

The carrier member 204 includes a second surface 216 that opposes the first surface 214. The carrier member 204 may have, for example, a circular, oval, or other cross-sectional shape. As such, "opposing surfaces" refers to the fact that at least a portion of each of the surfaces 214 and 216 faces in substantially opposing directions from one another. Carrier member 204 may be manufactured from a silicone material and is connected to a lead region (not shown in FIG. 2A) from the proximal region. The lead region physically and electrically connects stimulating lead assembly 218 with a stimulator unit (not shown in FIG. 2A).

The fixation feature 202 is configured to substantially prevent extrusion of the stimulating assembly 218 from the cochlea 240. In the embodiment of FIGS. 2A-2C, the fixation feature 202 is formed by a portion 250 of the carrier member 204 and a portion 252 of a shape element 254 permanently disposed in the carrier member 204. The fixation feature 202 is, in essence, a transition region in the stimulating assembly 218 that connects two offset segments (portions) of the stimulating assembly 218, namely a proximal or first portion 205 and a second or distal portion 207. The fixation feature 202 has a generally zigzag or sinuous shape.

As shown in FIG. 2C, following insertion of the stimulating assembly 218 into a recipient's cochlea, the fixation feature 202 is configured to engage an inner surface (wall) 227 of the cochlea 240 adjacent to an opening 274 (through which the stimulating assembly 218 is inserted) to prevent movement of the stimulating assembly out of the cochlea through the opening 274. The shape and mechanical properties of the fixation feature 202 cause a region 223 of surface 216 to abut the wall 227 within the cochlea 240. In this implanted position, the region 223 of surface 216 is substantially parallel to the wall 227, but is substantially perpendicular to a central axis 229 of the opening 274. As such, the fixation feature 202 operates with the cochlea wall 227 to resist/counteract forces from within the cochlea 240 towards opening 274.

As shown in greater detail in FIG. 2B, the portion 252 of shape element 254 comprises a first angle 260 and a second angle 262. The first angle 260 faces substantially away from first surface 214 of the stimulating assembly 218, while the second angle 262 faces substantially towards the first surface 214 of the stimulating assembly 218. That is, the first and second angles 260 and 262 face in substantially opposing directions forming a zigzag shape within shape element 254 at segment 252. Stated differently, the portion 252 comprises two substantially parallel and offset segments 255(A) and 255(B) connected by a third segment 257. Prior to insertion into a cochlea while in a steady (i.e., non-biased and non-stretched) state, the segments 255(A) and 255(B) are offset from one another by a distance 258.

The carrier member 204 is molded around the shape element 254 such that the portion 250 of the carrier member 204 has a shape corresponding to the shape of portion 252. That is, portion 250 comprises a first angle 270 and a second angle 272 generally corresponding to the first angle 260 and second angle 262, respectively, of shape element 254. The first and second angles 270 and 272 substantially oppose one another forming a zigzag pattern within carrier member 204 at portion 250.

In general, the angle 260 in FIG. 2B should be minimized in order to make insertion possible, while still providing sufficient function as a feature to prevent migration. In the example of FIG. 2B, angle 260 is approximately 150 degrees. In certain embodiments, the angle 260 may be in the range of approximately 160 degrees to approximately 170 degrees. As such, in certain embodiments, the angle 260 may be larger than angle 262.

It is to be appreciated that the lengths of segment 257 and fixation feature 202 shown in FIGS. 2A-2C are merely illustrative. In other embodiments, the segment 257 and fixation feature 202 may be relatively longer than as shown in FIGS. 2A-2C. The lengths of segment 257 and fixation 202 are generally selected to provide sufficient offset to enable the fixation feature 202 to interlock with a wall of the cochlea.

A surgeon inserts stimulating assembly 218 into cochlea 240 via an opening 274. The opening 274 may be, for example, the oval window, round window or other natural or man-made aperture (e.g., cochleostomy) in cochlea 240. In particular, the surgeon "pushes" the stimulating assembly 218 through the opening 274 in the direction of the apical end of the cochlea 240. In certain examples, the fixation feature 202 may be partially deformed from the zigzag shape so as to fit through the opening 274.

In terms of surgical technique, the surgeon will likely grip the stimulating assembly 218 at, or as close as possible to, the fixation feature 202 during most of the insertion. The surgeon may only grip proximal end 212 in the final stage to push the fixation feature 202 through the cochlea opening.

When the surgeon ceases to push the stimulating assembly 218 into the cochlea 240, the stimulating assembly 218 will have a tendency to migrate in the direction of the opening 274. This tendency may be the result of internal forces within the stimulating assembly 218 (i.e., elastic nature of the carrier member 204 and/or the electrical conductors disposed therein) and/or interaction of the stimulating assembly with the cochlea 240 that place bias force(s) on the stimulating assembly 218 in a proximal direction. The bias force(s) on stimulating assembly 218 are represented in FIG. 2C by arrow 277.

The shape element 254 is formed from a material having elastic properties such as a nitinol alloy or an elastomeric polymer such as silicone rubber. Due to the elastic nature of the shape element 254, the bias forces 277 cause the fixation feature 202 (i.e., portion 223 of surface 216) to be forced against wall 227 of the cochlea 240 that is adjacent to the opening 274. In this case, the portion 223 is substantially parallel to the wall 227 at a point between the opening 274 and the lateral wall 235 of the cochlea 240. The interaction of fixation feature 202 with the wall 227 of the cochlea 240 will counteract the bias forces 277 to prevent movement of the stimulating assembly 218 out of the cochlea through the opening 274.

In general, a stimulating assembly remains implanted in a recipient permanently. However, in certain circumstances, a stimulating assembly may be removed from a recipient during surgery (i.e., to reposition the stimulating assembly) or after a period of time. Although the fixation feature 202 is configured to prevent migration of the stimulating assembly 218 out of the cochlea 240, the fixation feature 202 does not prevent surgical removal of the stimulating assembly 218. More specifically, as noted above, the fixation feature 202 is configured such that the bias forces 277 force the fixation feature against the cochlea wall. However, when a surgeon places a tensile force on the proximal end 212 of the stimulating assembly 218, the elastic nature of the shape element 254, coupled with the zigzag shape, causes the fixation feature 202 to at least partially straighten and slide out of the cochlea through the opening 274. Therefore, the fixation feature 202 is configured to operate with the cochlea wall to resist/counteract forces from within the cochlea 240 towards opening 274, but is at least partially non-resistive to tensile forces placed on the stimulating assembly 218 outside of the cochlea 240.

It is also to be appreciated that the zigzag shape of fixation feature 202 shown in FIGS. 2A-2C is merely illustrative. Fixation feature 202 may have any other shape that, when inserted in the cochlea 240, causes a region of the lower surface (i.e., surface 216) to be substantially parallel to the wall 227 so as to operate with the cochlea wall 227 to resist/counteract forces from within the cochlea 240 towards opening 274, while still enabling removal of the stimulating assembly 218 (i.e., at least partially non-resistive to tensile forces placed on the stimulating assembly 218 outside of the cochlea 240).

Figure 3A:
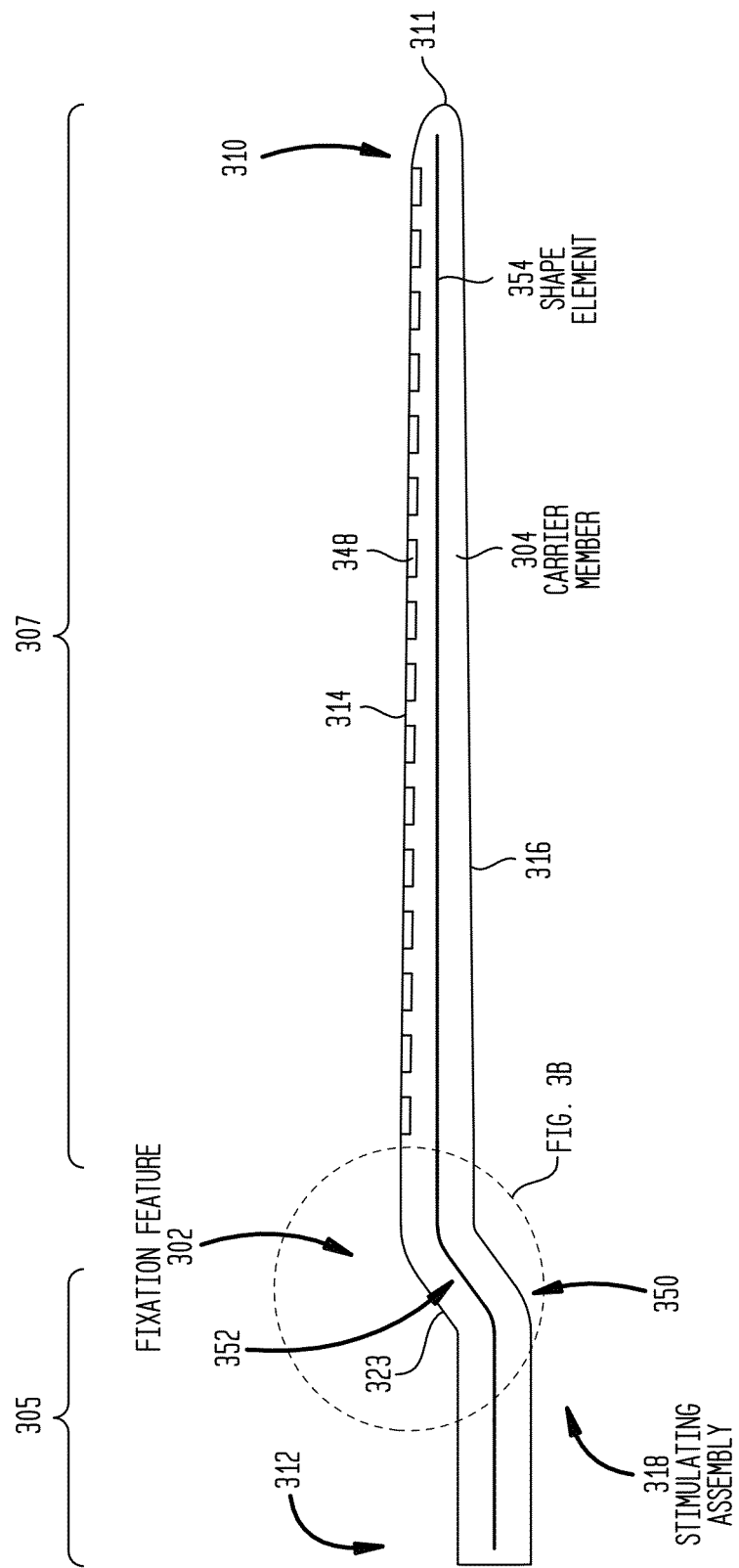
FIG. 3A is a side view of another stimulating assembly comprising a fixation feature in accordance with embodiments of the present invention.
Figure 3B:
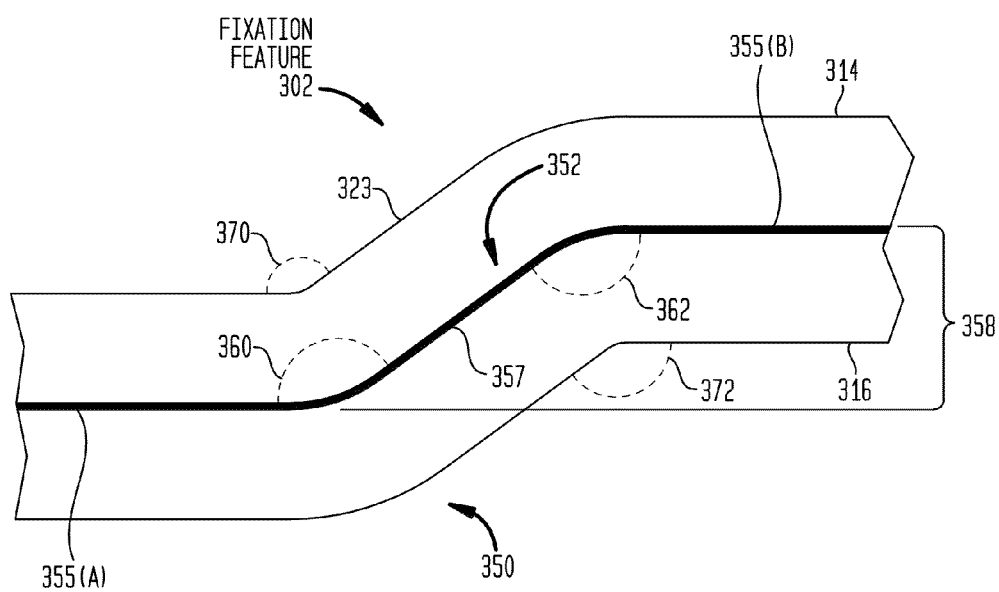
FIG. 3B is an enlarged view of the fixation feature of the stimulating assembly illustrated in FIG. 3A.
Figure 3C:
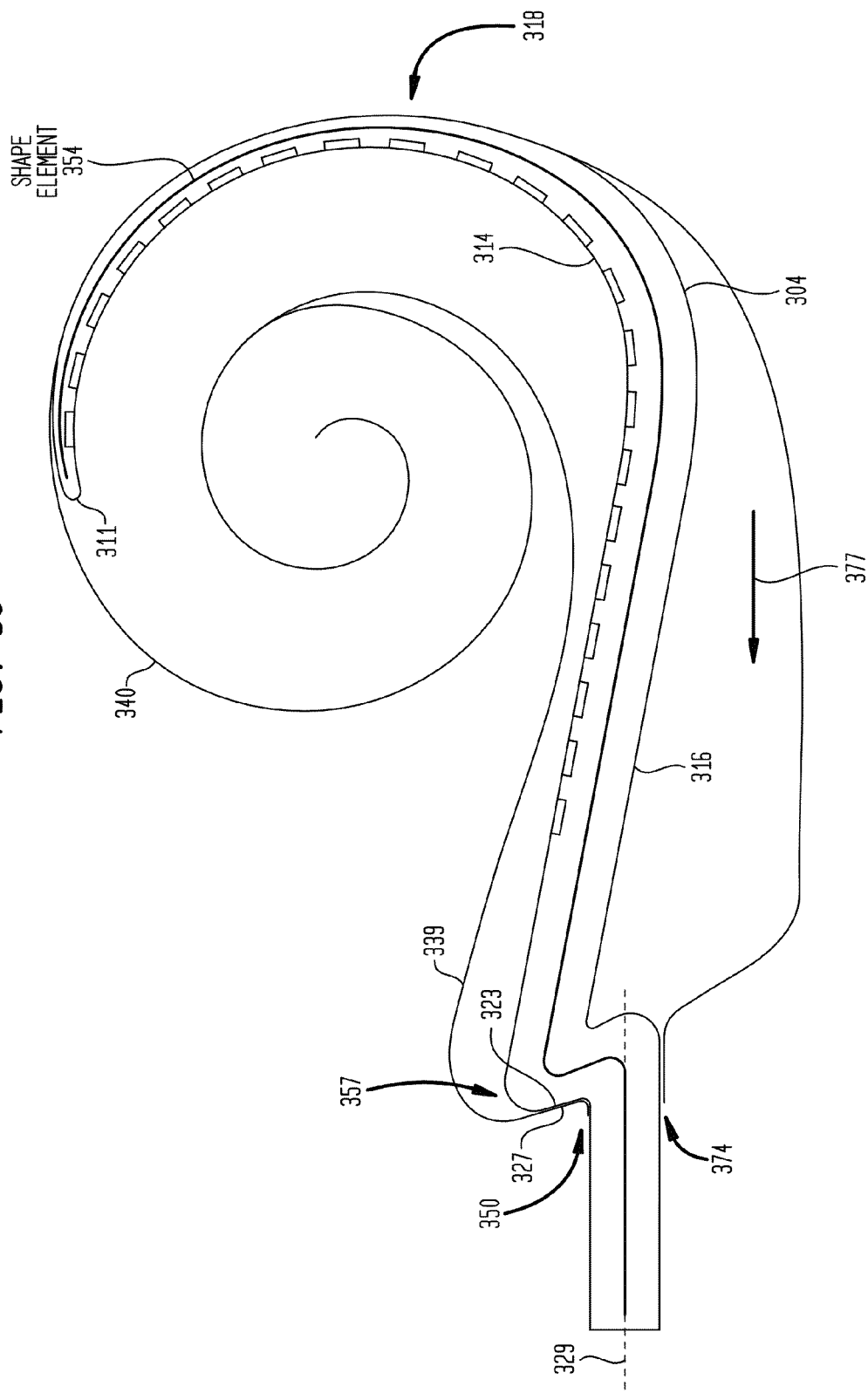
FIG. 3C is a side view of the stimulating assembly illustrated in FIG. 3A following insertion into a recipient's cochlea.

FIGS. 3A-3C are side views of another stimulating assembly 318 comprising a fixation feature 302 in accordance with embodiments presented herein. Fixation feature 302 is similar to fixation feature 202, but has an alternative zigzag shape.

FIG. 3A illustrates stimulating assembly 318 prior to insertion into a recipient's cochlea, while FIG. 3B illustrates an enlarged view of the fixation feature 302. FIG. 3C illustrates electrode assembly 318 after insertion when the fixation feature 302 is positioned to substantially prevent extrusion/migration of the stimulating assembly 318 out of the recipient's cochlea 340.

Stimulating lead assembly 318 comprises a carrier member 304 having a distal end 310 and a proximal end 312. Distal end 310 terminates in a tip 311 that is adapted to be implanted furthest into the recipient's cochlea 340. A plurality of spaced stimulating contacts 348 are mounted or disposed in/on at least a first surface 314 of the carrier member 304 between the proximal end 312 and the distal end 310.

The carrier member 304 includes a second surface 316 that opposes the first surface 314. The carrier member 304 may have, for example, a circular, oval, or other cross-sectional shape. Carrier member 304 may be manufactured from a silicone material and is connected to a lead region (not shown in FIG. 3A). The lead region physically and electrically connects stimulating lead assembly 318 with a stimulator unit (not shown in FIG. 3A).

The fixation feature 302 is configured to substantially prevent extrusion of the stimulating assembly 318 from the cochlea 340. In the embodiments of FIGS. 3A-3C, the fixation feature 302 is formed by a portion 350 of the carrier member 304 and a portion 352 of a shape element 354 permanently disposed in the carrier member 304. The fixation feature 302 is, in essence, a transition region in the stimulating assembly 318 that connects two offset segments (portions) of the stimulating assembly 318, namely a proximal or first portion 305 and a second or distal portion 307. The fixation feature 302 has a generally zigzag or sinuous shape.

As shown in FIG. 3C, following insertion of the stimulating assembly 318 in a recipient's cochlea, the fixation feature 302 is configured to engage an inner surface (wall) 327 of the cochlea 340 adjacent to an opening 374 (through which the stimulating assembly 318 is inserted) to prevent movement of the stimulating assembly out of the cochlea through the opening 374. The shape and mechanical properties of the fixation feature 302 cause a region 323 of surface 314 to abut the wall 327 within the cochlea 340. In this implanted position, the region 323 of surface 314 is substantially parallel to the wall 327, but is substantially perpendicular to a central axis 329 of the opening 374. As such, the fixation feature 302 operates with the cochlea wall 327 to resist/counteract forces from within the cochlea 340 towards opening 374.

As shown in greater detail in FIG. 3B, the portion 352 of shape element 354 comprises a first angle 360 and a second angle 362. The first angle 360 faces substantially towards the first surface 314 of the stimulating assembly 318, while the second angle 362 faces substantially away from first surface 314 of the stimulating assembly 318. That is, the first and second angles 360 and 362 face substantially opposing directions forming a zigzag pattern within shape element 354 at segment 352. Stated differently, the portion 352 comprises two substantially parallel and offset segments 355(A) and 355(B) connected by a third segment 357. Prior to implantation, the segments 355(A) and 355(B) are offset from one another by a distance 358.

The carrier member 304 is molded around the shape element 354 such that the portion 350 of the carrier member 304 has a shape corresponding to the shape of portion 352. That is, portion 350 comprises a first angle 370 and a second angle 372 generally corresponding to the first angle 360 and second angle 362, respectively, of shape element 354. The first and second angles 370 and 372 substantially oppose one another forming a zigzag pattern within carrier member 304 at portion 350.

In general, the angle 360 in FIG. 3B should be minimized in order to make insertion possible, while still providing sufficient function as a feature to prevent migration. In the example of FIG. 3B, angle 360 is approximately 150 degrees. In certain embodiments, the angle 360 may be in the range of approximately 160 degrees to approximately 170 degrees. As such, in certain embodiments, the angle 360 may be larger than angle 362.

It is also to be appreciated that the lengths of segment 357 and fixation feature 302 shown in FIGS. 3A-3C are merely illustrative. In other embodiments, the segment 357 and fixation feature 302 may be relatively longer than as shown in FIGS. 3A-3C. The lengths of segment 357 and fixation 302 are generally selected to provide sufficient offset to enable the fixation feature 302 to interlock with a wall of the cochlea.

A surgeon inserts stimulating assembly 318 into cochlea 340 via an opening 374. In particular, the surgeon "pushes" the stimulating assembly 318 through the opening 374 in the direction of the apical end of the cochlea 340. When the surgeon ceases to push the stimulating assembly 318 into the cochlea 340, the stimulating assembly 318 will have a tendency to migrate in the direction of the opening 374. This tendency may be the result of internal forces within the stimulating assembly 318 and/or interaction of the stimulating assembly with the cochlea 340 that place bias force(s) on the stimulating assembly 318 in a proximal direction. The bias force(s) on stimulating assembly 318 are represented in FIG. 3C by arrow 377.

In terms of surgical technique, the surgeon will likely grip the stimulating assembly 318 at, or as close as possible to, the fixation feature 302 during most of the insertion. The surgeon may only grip proximal end 312 in the final stage to push the fixation feature 302 through the cochlea opening.

The shape element 354 is formed from a material having elastic properties such as a nitinol alloy or an elastomeric polymer such as silicone rubber. As such, the bias forces 377 cause the zigzag shaped fixation feature 302 (i.e., portion 323 of surface 214) to be forced against a surface of the cochlea 340 that is adjacent to the opening 374. In this case, the portion 323 is substantially parallel to the wall 327 at a point between the opening 374 and the medial wall 339 of the cochlea 340. The interaction of fixation feature 302 with the wall 327 will counteract the bias forces 377 to prevent movement of the stimulating assembly 318 out of the cochlea through the opening 374.

Although the fixation feature 302 is configured to prevent migration of the stimulating assembly 318 out of the cochlea 340, the fixation feature 302 does not prevent surgical removal of the stimulating assembly 318. As noted above, the fixation feature 302 is configured such that the bias forces 377 push the fixation feature against the cochlea wall. However, when a surgeon places a tensile force on the proximal end 312 of the stimulating assembly 318, the elastic nature of the shape element 354 coupled with the zigzag shape causes the fixation feature 302 to at least partially straighten and slide out of the cochlea through the opening 374. Therefore, the fixation feature 302 is configured to operate with the cochlea wall to resist/counteract forces from within the cochlea 340 towards opening 374, but is at least partially non-resistive to tensile forces placed on the stimulating assembly 318 outside of the cochlea 340.

It is also to be appreciated that the zigzag shape of fixation feature 302 shown in FIGS. 3A-3C is merely illustrative. Fixation feature 302 may have any other shape that, when inserted in the cochlea 340, causes a region of the upper surface (i.e., surface 314) to be substantially parallel to the wall 327 so as to operate with the cochlea wall 327 to resist/ counteract forces from within the cochlea 340 towards opening 374, while still enabling removal of the stimulating assembly 318 (i.e., at least partially non-resistive to tensile forces placed on the stimulating assembly 318 outside of the cochlea 340).

FIGS. 2A-2C and 3A-3C illustrate fixation features that comprise a portion of a carrier member and a shape element disposed within the carrier member. In those embodiments, the shape element has elastic properties that enable the zigzag shaped fixation features to be forced against an inner surface of the cochlea following insertion. It is to be appreciated that the shape element may take a number of different arrangements. It is also to be appreciated that the shape element may be omitted in certain embodiments. Instead, the carrier member, or at least a portion thereof forming a fixation feature, may be formed to have the elastic properties and desired zigzag shape.

Figure 4A:
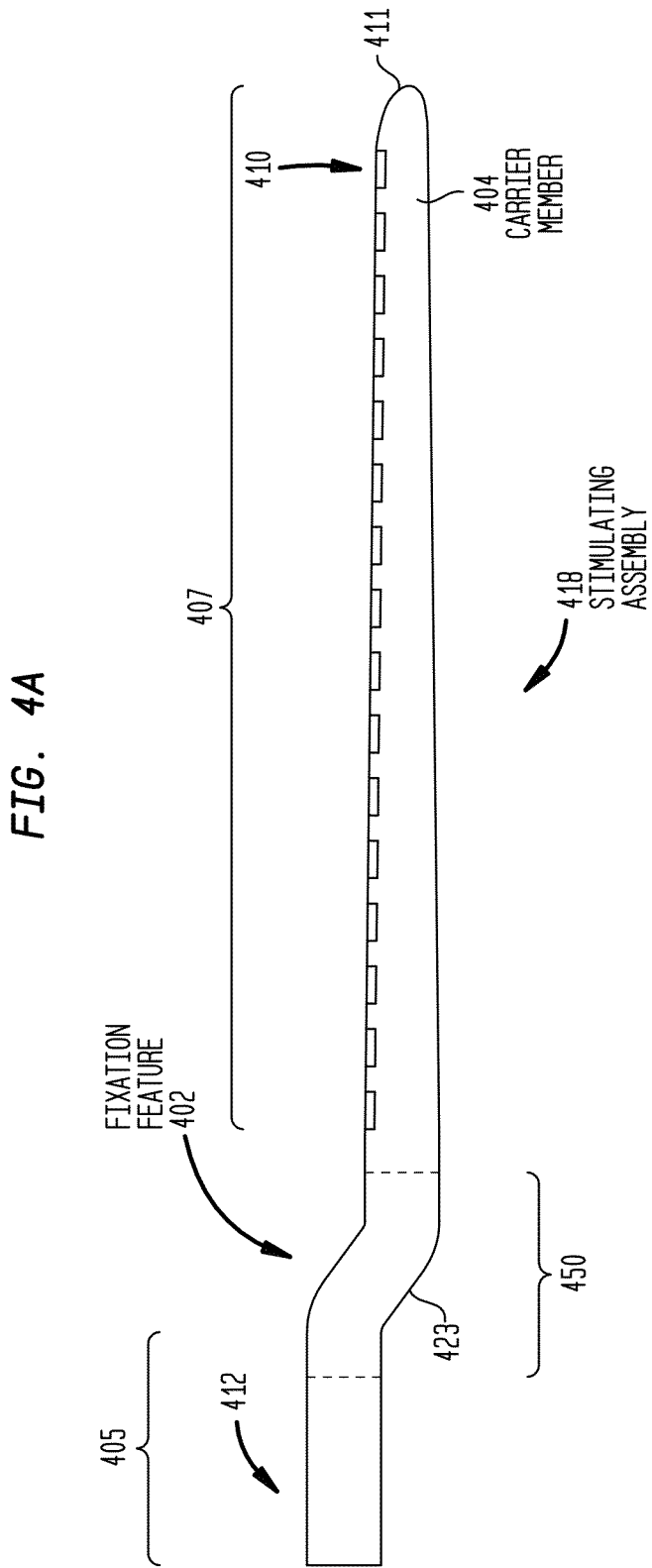
FIG. 4A is a side view of another stimulating assembly comprising a fixation feature in accordance with embodiments of the present invention.
Figure 4B:
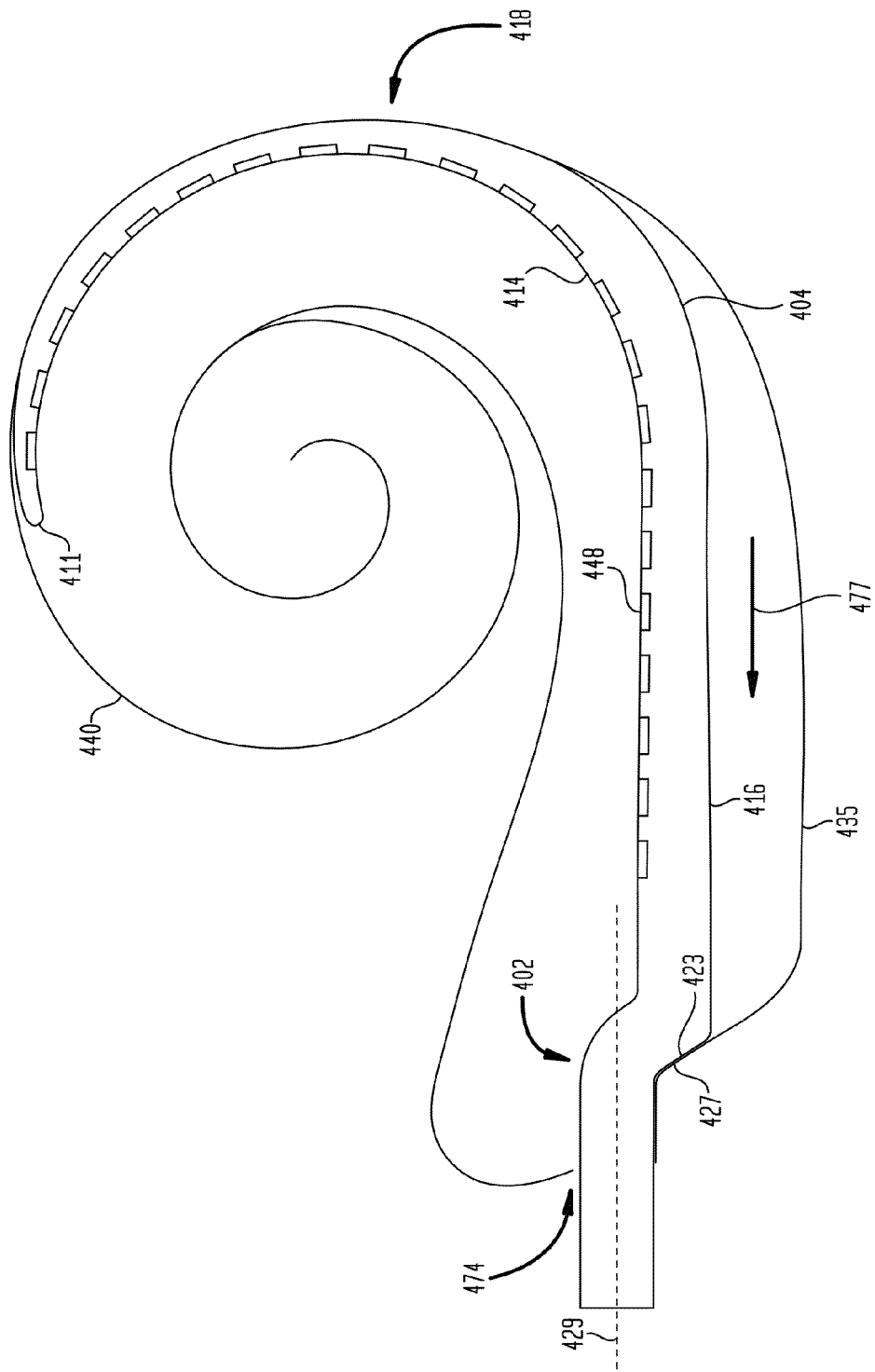
FIG. 4B is a side view of the stimulating assembly illustrated in FIG. 4A following insertion into a recipient's cochlea.

FIGS. 4A and 4B illustrate one such example of a stimulating assembly 418 having a fixation feature 402 formed without a shape element. FIG. 4A illustrates stimulating assembly 418 prior to insertion into a recipient's cochlea, while FIG. 4B illustrates electrode assembly 418 after insertion when the fixation feature 402 is positioned to substantially prevent extrusion/migration of the stimulating assembly 418 out of the recipient's cochlea 440.

In this example, the stimulating assembly 418 comprises a carrier member 404 having a distal end 410 and a proximal end 412. Distal end 410 terminates in a tip 411 that is adapted to be implanted furthest into the recipient's cochlea 440. A plurality of spaced stimulating contacts 448 are mounted or disposed in/on at least a first surface 414 of the carrier member 404 between the proximal end 412 and the distal end 410.

The carrier member 404 includes a second surface 416 that opposes the first surface 414. Carrier member 404 may be manufactured from one or more silicone materials and is connected to a lead region (not shown in FIG. 4A) from the proximal region. The lead region physically and electrically connects stimulating lead assembly 418 with a stimulator unit (not shown in FIG. 4A).

The fixation feature 402 is configured to substantially prevent extrusion of the stimulating assembly 418 from the cochlea 440. In the embodiment of FIGS. 4A and 4B, the fixation feature 402 is formed by a portion 450 of the carrier member 404. In this embodiment, the portion 450 is formed from silicone rubber. The grade of silicone used for portion 450 may have a greater stiffness than the grade of silicone used for the remainder of the stimulating assembly 418, which is designed to maximize flexibility for atraumatic insertion. In other words, different grades of silicone may be used for the portion 450 and the rest of the stimulating assembly 418.

As shown, the fixation feature 402 is, in essence, a transition region in the stimulating assembly 418 that connects two offset segments (portions) of the stimulating assembly 418, namely a proximal or first portion 405. The fixation feature 402 has a generally zigzag or sinuous shape.

As shown in FIG. 4B, following insertion of the stimulating assembly 418 in a recipient's cochlea, the fixation feature 402 is configured to engage an inner surface (wall) 427 of the cochlea 440 adjacent to an opening 474 (through which the stimulating assembly 418 is inserted) to prevent movement of the stimulating assembly out of the cochlea through the opening 474. The shape and mechanical properties of the fixation feature 402 cause a region 423 of surface 416 to abut the wall 427 within the cochlea 440. In this implanted position, the region 423 of surface 416 is substantially parallel to the wall 427, but is substantially perpendicular to a central axis 429 of the opening 474. As such, the fixation feature 402 operates with the cochlea wall 427 to resist/counteract forces from within the cochlea 440 towards opening 474.

It is to be appreciated that the lengths of fixation feature 402 shown in FIGS. 4A and 4B is merely illustrative. In other embodiments, the fixation feature 402 may be relatively longer than as shown in FIGS. 4A and 4B. The length of fixation feature 402 is generally selected to provide sufficient offset to enable the fixation feature 402 to interlock with a wall of the cochlea.

A surgeon inserts stimulating assembly 418 into cochlea 440 via the opening 474. The opening 474 may be, for example, the oval window, round window or other natural or man-made aperture (e.g., cochleostomy) in cochlea 240. In particular, the surgeon "pushes" the stimulating assembly 418 through the opening 474 in the direction of the apical end of the cochlea 440. In certain examples, the carrier member 204 includes a second surface 216 that opposes the first surface 214. The carrier member 204 may have, for example, a circular, oval, or other cross-sectional shape. As such, "opposing surfaces" refers to the fact that at least a portion of each of the surfaces 214 and 216 faces in substantially opposing directions from one another. Carrier member 204 may be manufactured from a silicone material and is connected to a lead region (not shown in FIG. 2A) from the proximal region. The lead region physically and electrically connects stimulating lead assembly 218 with a stimulator unit (not shown in FIG. 2A).

In terms of surgical technique, the surgeon will likely grip the stimulating assembly 418 at, or as close as possible to, the fixation feature 402 during most of the insertion. The surgeon may only grip proximal end 412 in the final stage to push the fixation feature 402 through the cochlea opening.

When the surgeon ceases to push the stimulating assembly 418 into the cochlea 440, the stimulating assembly 418 will have a tendency to migrate in the direction of the opening 474. This tendency may be the result of internal forces within the stimulating assembly 418 (i.e., elastic nature of the carrier member 244 and/or the electrical conductors disposed therein) and/or interaction of the stimulating assembly with the cochlea 440 that place bias force(s) on the stimulating assembly 418 in a proximal direction. The bias force(s) on stimulating assembly 418 are represented in FIG. 4B by arrow 477.

Due to the mechanical properties of the fixation feature 402, the bias forces 477 cause the fixation feature 402 (i.e., portion 423 of surface 416) to be forced against wall 427 of the cochlea 440 that is adjacent to the opening 474. In this case, the portion 423 is substantially parallel to the wall 427 at a point between the opening 474 and the lateral wall 435 of the cochlea 440. The interaction of fixation feature 402 with the wall 427 of the cochlea 440 will counteract the bias forces 477 to prevent movement of the stimulating assembly 418 out of the cochlea through the opening 474.

In general, a stimulating assembly remains implanted in a recipient permanently. However, in certain circumstances, a stimulating assembly may be removed from a recipient during surgery (i.e., to reposition the stimulating assembly) or after a period of time. Although the fixation feature 402 is configured to prevent migration of the stimulating assembly 418 out of the cochlea 440, the fixation feature 402 does not prevent surgical removal of the stimulating assembly 418. More specifically, as noted above, the fixation feature 402 is configured such that the bias forces 477 force the fixation feature against the cochlea wall. However, when a surgeon places a tensile force on the proximal end 412 of the stimulating assembly 418, the mechanical properties and/or shape of the fixation feature 402 cause the fixation feature 402 to at least partially straighten and slide out of the cochlea through the opening 474. Therefore, the fixation feature 402 is configured to operate with the cochlea wall to resist/counteract forces from within the cochlea 440 towards opening 474, but is at least partially non-resistive to tensile forces placed on the stimulating assembly 418 outside of the cochlea 440.

It is also to be appreciated that the zigzag shape of fixation feature 402 shown in FIGS. 4A and 4B is merely illustrative. Fixation feature 402 may have any other shape that, when inserted in the cochlea 440, causes a region of the lower surface (i.e., surface 416) to be substantially parallel to the wall 427 so as to operate with the cochlea wall 427 to resist/counteract forces from within the cochlea 440 towards opening 474, while still enabling removal of the stimulating assembly 418 (i.e., at least partially non-resistive to tensile forces placed on the stimulating assembly 418 outside of the cochlea 440).

FIG. 4C illustrates an example where the fixation feature 402 is held straight for insertion into a recipient's cochlea by a sheath 457. As shown, the sheath 457 extends around (i.e., partially envelopes) at least the portion 450 and has sufficiently rigidity to maintain the portion 450 in a relatively straight configuration for insertion into the recipient's cochlea. The sheath 457 may be formed from a material that is relatively stiffer than the material forming portion 450.

In certain embodiments, the sheath 457 is configured to be removed during or after insertion to so as to enable the portion 450 to adopt the shape shown in FIG. 4A. For example, the sheath may be a split tube that supports the portion 450 in a substantially straight configuration during insertion. The sheath 457 may be removed as the portion 450 passes through opening 474 (FIG. 4B) or may be removed after portion 450 passes through the opening.

In other embodiments, the sheath 457 is formed from a bioresorbable material which softens or dissolves on exposure to the recipient's body fluid. More specifically, the sheath 457 may be configured to soften or dissolve upon insertion into the cochlea so as to enable the portion 450 to adopt the shape shown in FIG. 4A (i.e., to interlock with the cochlea). In such embodiments, the bioresorbable material forming the sheath 457 may be selected from, for example, polyacrylic acid (PAA), polyvinyl alcohol (PVA), polylactic acid (PLA) and polyglycolic acid (PGA).

In a still further embodiment, the sheath 457 can be formed from a shape memory alloy or a heat sensitive material. For example, the stiffening element can be formed from a nickel/titanium alloy, or a bimetallic element formed of a laminate of two different metals, that is shaped to take a straight or substantially straight configuration at room temperature but bends into another shape once it is exposed to body temperature.

It is to be appreciated that the use of sheath 457 with stimulating assembly 418 is merely illustrative. The sheath 457, or other sheaths, may be use with other stimulating assemblies described herein to maintain fixation features in a relatively straight configuration during insertion into a recipient's cochlea.

Figure 5A:
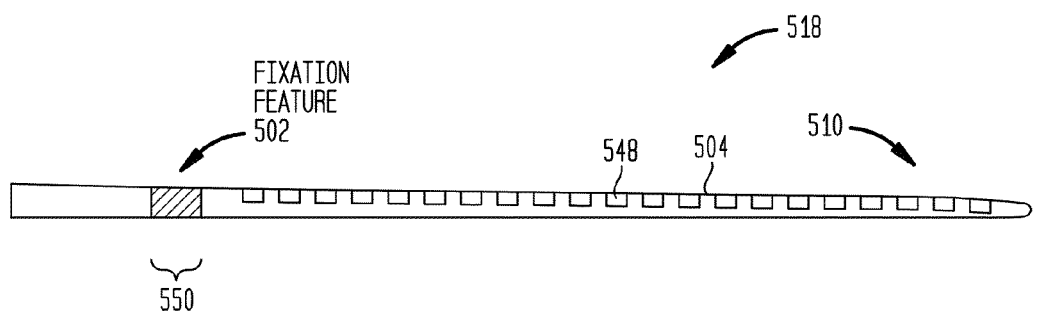
FIG. 5A is a side view of a stimulating assembly comprising a fixation feature in accordance with embodiments of the present invention.
Figure 5B:
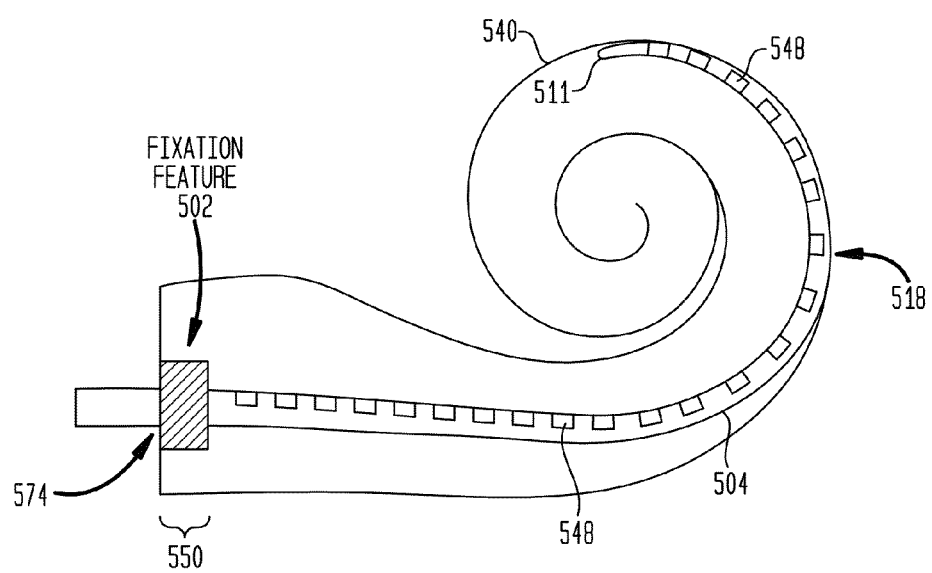
FIG. 5B is a side view of the stimulating assembly illustrated in FIG. 5A following insertion into a recipient's cochlea.

FIGS. 5A and 5B are side views of an embodiment of an electrode assembly 518 comprising an expandable fixation feature 502. FIG. 5A illustrates the stimulating assembly 518 and expandable fixation feature 502 prior to insertion into a recipient's cochlea, while FIG. 5B illustrates the stimulating assembly 518 and expandable fixation feature 502 after insertion into the cochlea.

Stimulating lead assembly 518 comprises a carrier member 504 having a distal end 510 and a proximal end 512. A plurality of spaced-apart stimulating contacts 548 is disposed on or in a carrier member 504. As shown in FIG. 5B, stimulating lead assembly 518 may be implanted into cochlea 540 through an opening 574 in a cochlea 540. The aperture may be, for example, the oval window, round window, or a cochleostomy, as described above.

The expandable fixation feature 502 comprises a portion 550 of carrier member 504 that has a first configuration that enables the fixation feature 502 to be inserted into a recipient's cochlea via an opening 574. The portion 550 of the stimulating assembly 518 is configured to swell when exposed to the recipient's bodily fluid (i.e., the recipient's cochlea fluid). As such, after insertion into the cochlea, the portion 550 has a second configuration where the portion engages an inner surface of the cochlea adjacent to the opening so as to prevent movement of the stimulating assembly 518 out of the cochlea.

As noted above, the portion 550 is formed from a material that expands (e.g., swells) upon exposure to the recipient's cochlea fluid. The remainder of the stimulating assembly 518 is formed from a polymeric material that does not expand when exposed to cochlea fluid. In certain embodiments, the entirety of portion 550 is formed from the expandable material, while in other embodiments only an outer region of the portion 550 is formed from the expandable material.

Figure 6A:
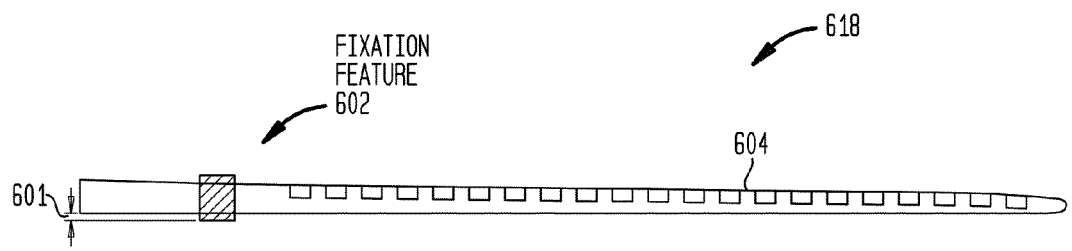
FIG. 6A is a side view of a stimulating assembly comprising a fixation feature in accordance with embodiments of the present invention.
Figure 6B:
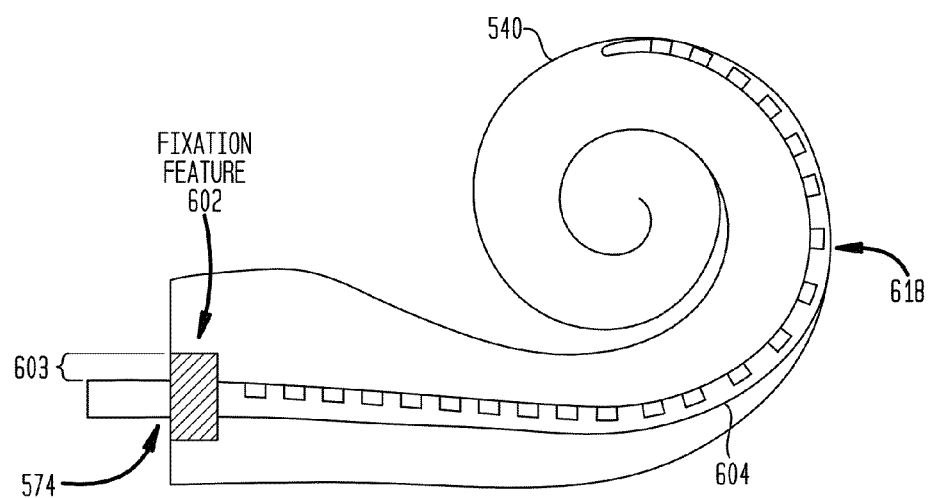
FIG. 6B is a side view of the stimulating assembly illustrated in FIG. 5A following insertion into a recipient's cochlea.

FIGS. 6A and 6B illustrate further embodiments presented herein where a stimulating assembly 618 comprises an expandable fixation feature 602 formed by positioning or molding an expandable material around the outer surface of a carrier member 604. In such embodiments, the expandable fixation feature 602 has a pre-insertion thickness and a different post-insertion thickness. That is, in the pre-insertion configuration of FIG. 6A, the expandable fixation feature 602 extends from the outer surface of carrier member 604 by a distance 601. However, in the post-insertion configuration of FIG. 6B, the expandable fixation feature 602 has a thickness 603 that is greater than the thickness 601.

The expandable materials used in the embodiments of FIGS. 5A-5B and 6A-6B may be a biocompatible hygroscopic material such as soft hygroscopic polymeric or hydrogel material. As an example, the biocompatible material can be a natural polymer such as a glycosaminoglycan, for example, hyaluronic acid, chondroitin sulfate, and cellulose or a synthetic polymer, such as a hydrogel, poly(vinyl alcohol), poly(2-hydroxyethylmethylacrylate), and polyethylene oxide. Other possible materials include Polydimethylsiloxane (PDMS) elastomers, collagen, chitosan, alginate, a poly(acrylonitrile)-based hydrogel, poly(ethylene glycol)/poly(acrylic acid) (PEG/PAA) interpenetrating polymer network (IPN) hydrogel, polyethylene oxide-polybutylene terephthalate (PEO-PBT), a hyaluronic acid based hydrogel, high-molecular-weight polyacrylic acid (PAA) as a filler in a Silastic matrix, PVA/chitosan blends, poly(hydroxy ethylmethacrylate), poly(ethylene glycol) (PEG) hydrogels, tetraethylene glycol diacrylate, polyethylene glycol methacrylate (PEGMA), cross-linkable (2-hydroxyethyl methacrylate) (HEMA), and poly(methyl acrylate-co-hydroxyethyl acrylate) hydrogel. The use of a soft polymeric material, which may stretch and thin, may be beneficial should the stimulating lead assemblies 518/618 need to be surgically explanted.

Figure 7:
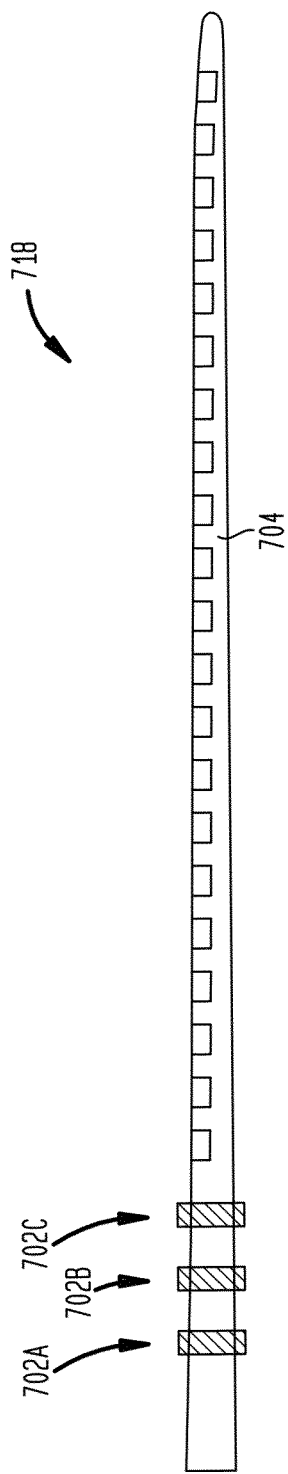
FIG. 7 is a side view of a stimulating assembly comprising a plurality of fixation features in accordance with embodiments of the present invention.

FIG. 7 illustrates a further embodiment of the present invention in which a plurality of expandable fixation features are provided. More specifically, FIG. 7 illustrates a stimulating assembly 718 comprising three expandable fixation features 702(A), 702(B), and 702(C). For ease of illustration, the three expandable fixation features 702(A), 702(B), and 702

(C) are each shown in a deployed or expanded (i.e., post-insertion) configuration. The expandable fixation features 702(A), 702(B), and 702(C) may formed by positioning or molding an expandable material around the outer surface of a carrier member 704 (as in the embodiments of FIGS. 6A and 6B), or may comprise a portion of the carrier member 704 (as in the embodiments of FIGS. 7A and 7B).

In general, the three expandable fixation features 702(A), 702(B), and 702(C) are present to provide a surgeon with the ability to select one of several final positions for the stimulating assembly 718. Each of the three expandable fixation features 702(A), 702(B), and 702(C) is configured to be inserted into a recipient's cochlea and expand into an expanded configuration. In the expanded configuration, each of the expandable fixation features 702(A), 702(B), and 702 (C) can operate with an inner surface of the cochlea to prevent migration of the stimulating assembly 718 from the cochlea.

FIGS. 5A-5B, 6A-6B, and FIG. 7 illustrate embodiments in which the expandable fixation features 502 and 602 expand substantially radially within the recipient's cochlea to form an annular flange. It is to be appreciated that the annular flange shape of FIGS. 5A-5B and 6A-6B is merely illustrative and that other shapes may be used in embodiments of the present invention (e.g., a toroidal shape).

Figure 8B:
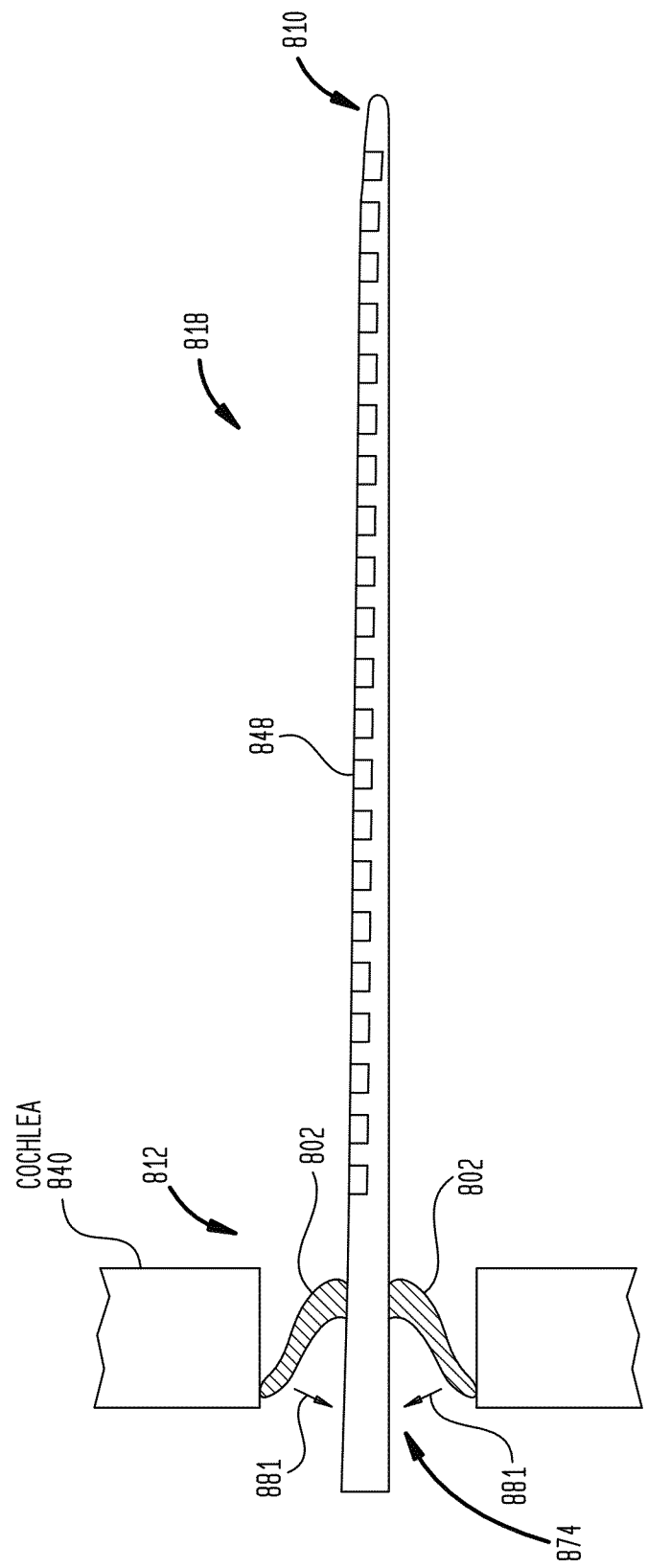
FIG. 8B is a side view of the stimulating assembly illustrated in FIG. 8A during insertion into a recipient's cochlea.

FIGS. 8A-8C are side views of a stimulating assembly 818 having alternative fixation features in accordance with embodiments of the present invention. FIG. 8A illustrates stimulating assembly 818 prior to insertion into a recipient's cochlea, while FIG. 8B illustrates electrode assembly 818 during insertion into a recipient's cochlea. FIG. 8C illustrates electrode assembly 818 after insertion when the fixation features are positioned to substantially prevent extrusion/migration of the stimulating assembly 818 out of the recipient's cochlea.

In the embodiments of FIGS. 8A-8C, the stimulating assembly 818 comprises a carrier member 804 having a distal end 810 and a proximal end 812. A plurality of stimulating contacts 848 is disposed in the carrier member 804. As shown, the stimulating assembly 818 is configured to be inserted through an opening 874 in a recipient's cochlea 840.

The stimulating assembly 818 also comprises a compressible fixation feature 802 extending around a circumference of a proximal end of the carrier member 804. For ease of illustration, the fixation feature 802 is shown in cross-section.

The fixation feature 802 comprises a circumferential flexible flange or collar formed from, for example, silicone, polyimide or PEEK, mesh (e.g., Dacron), or resilient or elastic metals. In certain examples, the non-silicone materials may form the body of the fixation feature 802, but are encased in a thin layer of silicone.

Prior to insertion, the fixation feature 802 extends out from the surface of the carrier member 804. However, the fixation features 802 have a shape and/or orientation so as to be compressed during insertion into a recipient's cochlea. More specifically FIG. 8B illustrates stimulating assembly 818 as surgeon pushes the stimulating assembly through an opening 874 in a recipient's cochlea 840. As the fixation feature 802 passes through the opening 874, the fixation feature bends backwards (i.e., in a proximal direction) toward the carrier member 804. That is, the walls of the opening 874 force the fixation feature 802 backwards in the direction generally shown by arrows 881.

Furthermore, as shown in FIG. 8C, due to the resilient/elastic properties of the fixation feature 802, the fixation feature is configured to return to its pre-insertion configuration after passing through the opening 874. That is, as generally shown by arrows 883, the fixation feature 802 "springs" outward or away from the carrier member 804 to return to the pre-insertion configuration once the fixation feature is positioned within the cochlea.

Similar to the embodiments described above, when the surgeon ceases to push the stimulating assembly 818 into the cochlea 840, the stimulating assembly 818 will have a tendency to migrate in the direction of the opening 874. This tendency may be the result of internal forces within the stimulating assembly 818 and/or interaction of the stimulating assembly with the cochlea 850 that place bias force(s) on the stimulating assembly 818 in a proximal direction.

As shown in FIG. 8C, the bias force(s) on stimulating assembly 818, which are represented in FIG. 8C by arrow 877, cause the fixation feature 802 to be forced against surfaces 895 of the cochlea 840 adjacent to the opening 874. In turn, the surfaces 895 place forces on the fixation feature 802 in the distal direction. The distal force(s) are represented in FIG. 8C by arrows 897. Although the fixation feature 802 is configured to bend backwards (i.e., in the proximal direction the carrier member 804), the fixation feature has sufficient rigidity such that they do not bend in the forward (distal) direction in response to the forces 897. As such that the engagement of the fixation feature with the surfaces 895 will counteract the bias forces 877 to prevent movement of the stimulating assembly 818 out of the cochlea through the opening 874.

Although the fixation feature 802 is configured to prevent migration of the stimulating assembly 818 out of the cochlea 840, the fixation feature 802 does not prevent surgical removal of the stimulating assembly 818. As noted above, the fixation feature 802 is configured such that the bias forces 877 push the fixation feature 802 against the cochlea wall and the fixation feature 802 has sufficient rigidity to resist bending in the forward direction. However, when a surgeon places sufficient tensile force on the proximal end 812 of the stimulating assembly 818 the fixation feature 802 may bend forward as it passes through the opening 874. Therefore, the fixation feature 802 is configured to operate with the cochlea wall to resist/counteract forces from within the cochlea 840 towards opening 874, but is non-resistive to tensile forces placed on the stimulating assembly 818 outside of the cochlea 840.

FIGS. 8A-8C illustrate a specific arrangement that uses compressible fixation features in the form of a single compressible flange. It is to be appreciated that other arrangements are within the scope of the present invention. For example, in alternative embodiment a two opposing flanges may be disposed on opposing sides of carrier member and operate substantially the same as described with reference to the flange of FIGS. 8A-8C. In other embodiments, more than two flanges may be used.

FIG. 9 illustrates a further embodiment of the present invention in which a plurality of compressible fixation features are provided. More specifically, FIG. 9 illustrates a stimulating assembly 918 comprising three compressible fixation features 902, 903, and 905. Each set 902, 903, and 905 comprises a circumferential flange configured as described above with reference to FIGS. 8A-8C.

In general, the three compressible fixation features 902, 903, and 905 are present to provide a surgeon with the ability to select one of several final positions for the stimulating assembly 918. Each of the three compressible fixation features 902, 903, and 905 are configured to be compressed during insertion to a recipient's cochlea and return to their original configuration thereafter. In the expanded configuration, each compressible fixation feature 902, 903, and 905 can operate with an inner surface of the cochlea to prevent migration of the stimulating assembly 918 from the cochlea.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A stimulating assembly for insertion into a cochlea of a recipient through an opening in the cochlea, comprising:
   an elongate carrier member having a proximal end and a distal end;
   a plurality of stimulating contacts disposed along at least a first surface of the carrier member; and
   a fixation feature formed in the proximal end of the carrier member configured to, after insertion into the cochlea, prevent movement of the stimulating assembly out of the cochlea through the opening,
   wherein the fixation feature has an initial generally straight configuration to facilitate insertion through the opening in a recipient's cochlea, and wherein the fixation feature has elastic properties so as to assume a general zigzag shape after insertion into the cochlea.

2. The stimulating assembly of claim 1, wherein the fixation feature has elastic properties and a shape such that forces in the direction of the opening force the fixation feature in contact with an inner surface of the cochlea between the opening and a lateral wall of the cochlea.

3. The stimulating assembly of claim 1, wherein the fixation feature has elastic properties and a shape such that forces in the direction of the opening force the fixation feature in contact with an inner surface of the cochlea between the opening and a medial wall of the cochlea.

4. The stimulating assembly of claim 1, wherein the fixation feature comprises a portion of the carrier member formed into a zigzag shape.

5. The stimulating assembly of claim 4, further comprising:
   a shape element permanently disposed in the carrier member,
   wherein the fixation feature further comprises a portion of the shape element formed into a zigzag shape that is disposed in the zigzag shaped portion of the carrier member.

6. The stimulating assembly of claim 5, wherein the shape element is a nitinol alloy wire.

7. The stimulating assembly of claim 1, further comprising:
   a sheath disposed around the fixation feature configured to retain the fixation feature in the generally straight configuration during insertion through the opening.

8. An apparatus, comprising:
   an elongate carrier member having first and second distally extending portions; and
   a plurality of stimulating contacts disposed along at least a first surface of the second portion,
   wherein the carrier member comprises a transition region having a shape such that the second portion of the elongate carrier member is offset from the first portion of the carrier member, and
   wherein the elongate carrier member is an intra-cochlea carrier member and the transition region is configured so that, after insertion into a recipient's cochlea, the transition region prevents movement of the apparatus out of the cochlea.

9. The apparatus of claim 8, wherein the transition region comprises a portion of the carrier member formed into a zigzag shape.

10. The apparatus of claim 8, further comprising:
    a nitnol shape element permanently disposed in the carrier member, wherein the nitnol shape element is configured to assume a zigzag shape following insertion into a recipient's cochlea.

11. The apparatus of claim 8, wherein the transition region has an initial generally straight configuration to facilitate insertion through an opening in a recipient's cochlea, and wherein the transition region has elastic properties so as to assume a zigzag shape after insertion into the cochlea.

12. The apparatus of claim 11, further comprising:
    a sheath disposed around the transition region configured to retain the transition region in the generally straight configuration during insertion through the opening.

13. The apparatus of claim 8, wherein the carrier member is configured to be inserted into a recipient's cochlea via an opening, and wherein the transition region has elastic properties and a shape such that forces in the direction of the opening force the transition region in contact with an inner surface of the cochlea between the opening and a lateral wall of the cochlea.

14. The apparatus of claim 8, wherein the carrier member is configured to be inserted into a recipient's cochlea via an opening, and wherein the transition region has elastic properties and a shape such that forces in the direction of the opening force the transition region in contact with an inner surface of the cochlea between the opening and a medial wall of the cochlea.

15. A stimulating assembly for implantation into a cochlea of a recipient through an opening in the cochlea, comprising:
    an elongate carrier member having a proximal portion and a distal portion;
    a plurality of stimulating contacts disposed along at least a first surface of the distal portion; and
    a fixation feature comprising a portion of the carrier member formed into a zigzag shape such that the distal portion of the elongate carrier member is offset from the proximal portion of the carrier member,
    wherein the fixation features is configured so that, after insertion into a recipient's cochlea, the zigzag shape prevents movement of the stimulating assembly out of the cochlea through the opening.

16. The stimulating assembly of claim 15, wherein the fixation feature has elastic properties and a shape such that forces in the direction of the opening force the fixation feature in contact with an inner surface of the cochlea between the opening and a lateral wall of the cochlea.

17. The stimulating assembly of claim 15, wherein the fixation feature has elastic properties and a shape such that forces in the direction of the opening force the fixation feature in contact with an inner surface of the cochlea between the opening and a medial wall of the cochlea.

18. The stimulating assembly of claim 15, further comprising:
    a shape element permanently disposed in the carrier member,
    wherein the fixation feature further comprises a portion of the shape element formed into a zigzag shape that is disposed in the zigzag shaped portion of the carrier member.

19. The stimulating assembly of claim 18, wherein the shape element is a nitinol alloy wire.

* * * * *